US008080213B2

(12) United States Patent  (10) Patent No.: US 8,080,213 B2
Sutton  (45) Date of Patent: Dec. 20, 2011

(54) OZONE GENERATOR AND METHOD FOR MAKING AND USING SAME

(76) Inventor: S. Jepson Sutton, Phoenix, AZ (US)

( * ) Notice: Subject to any disclaimer, the term of this patent is extended or adjusted under 35 U.S.C. 154(b) by 747 days.

(21) Appl. No.: 12/220,057

(22) Filed: Jul. 21, 2008

(65) Prior Publication Data

US 2010/0015013 A1    Jan. 21, 2010

(51) Int. Cl.
*B01J 19/08*    (2006.01)
(52) U.S. Cl. ............... 422/186.07; 422/186.3; 422/120; 422/121; 96/264; 250/461.1
(58) Field of Classification Search ............. 422/186.07, 422/186.3, 120, 121; 96/264; 250/461.1
See application file for complete search history.

(56) References Cited

U.S. PATENT DOCUMENTS

| 5,902,552 | A  | * | 5/1999 | Brickley ...................... 422/121 |
| 2003/0133832 | A1 | * | 7/2003 | D'Ottone ........................ 422/29 |
| 2006/0144689 | A1 | * | 7/2006 | Barnes et al. ............. 204/157.5 |

* cited by examiner

*Primary Examiner* — Jeffrey T Barton
*Assistant Examiner* — Xiuyu Tai (57) ABSTRACT

One embodiment of an improved ozone generator is comprehensively disclosed by descriptions of computer generated drawings depicting the first commercial version of the invention, which combines the following features: an extruded base with longitudinal channels for receiving connections at distributed points; an extruded cover for detachably engaging the base at each opposing sides and covering a substantial portion of said base; a central baffle that is integral with the cover fro dividing the enclosed volume into a reaction chamber and a circuitry chamber; one or more ultraviolet light sources mounted to connection points on a channel within the reaction chamber; electronic circuitry mounted to connection points on a channel within the circuitry chamber for controlling and transforming an input voltage to drive the light sources; sliding end caps secured to channels in the base for separately covering apertures formed by the ends of the cover and base and for detachably connecting the cover to the base; and a selectively restricted outlet conduit for providing fluid communication between the reaction chamber and an external point of ozone injection.

16 Claims, 6 Drawing Sheets

Informal Drawings: Ozone Generator and Method for Making and Using Same

S. Jepson Sutton

Informal Drawings: Ozone Generator and Method for Making and Using Same

S. Jepson Sutton

Informal Drawings: Ozone Generator and Method for Making and Using Same

S. Jepson Sutton

Informal Drawings: Ozone Generator and Method for Making and Using Same

S. Jepson Sutton

Informal Drawings: Ozone Generator and Method for Making and Using Same

S. Jepson Sutton

OZONE GENERATOR AND METHOD FOR MAKING AND USING SAME

BACKGROUND

The invention relates to an improved ozone generator for use in water treatment and other applications and, more particularly, an ultraviolet ozone generator that can accommodate different light sources to more effectively produce a range of ozone outputs matched to individual demand, that produces higher peak levels of ozone output and that can be made and used with greater cost-effectiveness, reliability and simplicity.

Ozone is well-known as a highly effective oxidization agent frequently used in a range of sanitation applications. It is particularly effective in the treatment of water. In cases where large volumes of ozone are required, methods such as corona discharge and cold plasma are preferred. However, smaller volumes of ozone can be very effectively and efficiently generated over time through the controlled exposure of ambient air (containing oxygen) to moderately intense ultraviolet radiation.

Ultraviolet ozone generators utilize one or more ultraviolet lamps, which generate light having a wave length distribution mostly in the 185 nm range. When air is passed over an ultraviolet lamp a portion of the oxygen ($O_2$) molecules in the gas are split. The resulting oxygen atoms ($O_1$), seeking stability, attach to oxygen molecules, forming ozone ($O_3$). The output gas from the generator is injected into the water being treated and the ozone in the gas inactivates, by oxidation, organic contaminants. Ozone also produces flocculation of suspended contaminants into clusters that can be more readily removed by passing the flow through an in-line filter.

Ultraviolet ozone generators have been used in the past to treat circulated water in swimming pools and spas. Two examples of prior art ozone generators designed for use in treating swimming pool water are the "QuikPure2" manufactured and sold by A&A Manufacturing of Phoenix Ariz. and the Paramount "Modular Ozone Generator" described in U.S. Patent Application Publication 2006/0144689A1. However these generators have been limited in their range of applications, have been inefficient in terms of peak ozone production, have been expensive and inconvenient to manufacture and have been difficult to service in the field. The object of the present invention is to overcome these shortcomings.

SUMMARY OF THE INVENTION

An ultraviolet ozone generator including an extruded base having a plurality of channels and an extruded cover that is detachably connected to the base in cooperation with two opposing end caps that engage the channels and enclose one or more ultraviolet light sources in one internal chamber and electronic circuitry to drive and control the light sources in another internal chamber, the end caps, bulbs and circuitry being secured to the base by connections to the channels therein, as more fully described in the claims appended to this specification.

DESCRIPTION OF THE DRAWINGS

Most of the accompanying drawings that depict assembled portions of the invention are derived from the same CAD drawings used to guide the actual production of the preferred embodiment described in detail in the following section.

DESCRIPTION OF PREFERRED EMBODIMENT

Basic Elements

Figures 1, 2:
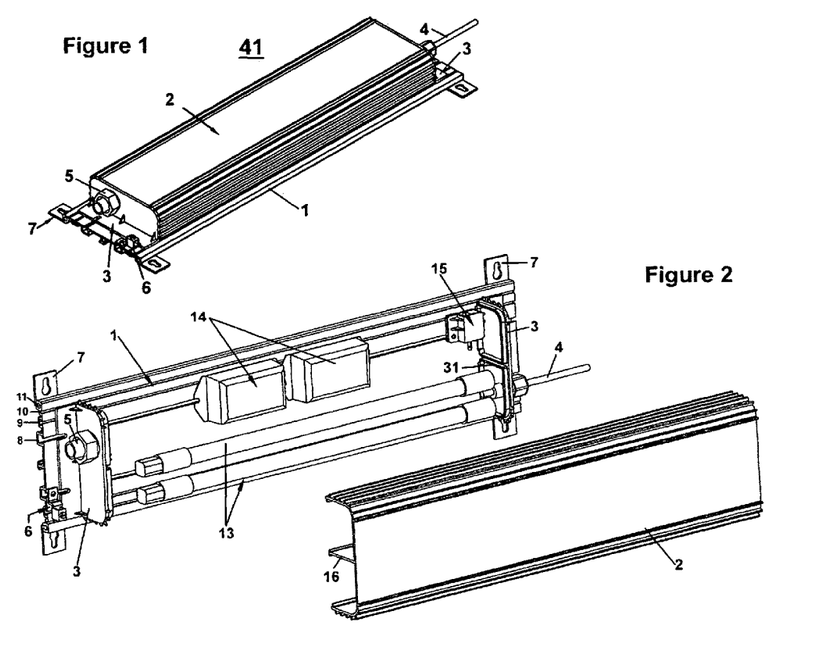
FIG. 1 is an external view of the preferred embodiment showing the main external features.
FIG. 2 shows the internal portion of the preferred embodiment with the cover removed to an adjacent position.

FIG. 1 provides an overview of the principal structural elements of the preferred embodiment of the present invention. The ozone generator 41 is constructed from an extruded base 1 that is characterized by a plurality of longitudinal channels 8, 9, 10 and 11 as more fully illustrated in FIGS. 2-3 and 5-7. An extruded cover 2 extends most of the length of the base l and is enclosed by opposing end caps 3, which also serve to lock the cover 2 firmly into place on the base 1. While the base 1 and cover 2 in the preferred embodiment were extruded from aluminum, these components could also be extruded from thermoplastic materials having excellent resistance to ozone and ultraviolet light.

FIG. 2 provides a perspective view of the internal components and structural elements included in one embodiment of the invention as seen with the cover 2 removed from the base 1. In this embodiment there are two ultraviolet tubes 13, each separately connected to the output side of corresponding ballast 14, which is, in turn, connected to a source of electrical power. For visual simplicity, the wires interconnecting the electrical components are not shown in any of the drawings, except the wiring diagram of FIG. 8.

FIGS. 1 and 2 show the location of an electrical feedthrough 5, which secures and protects the wires connected between an external source of 110 or 220 VAC power and the internal electronics of the ozone generator. An electrical ground lug 6 may be incorporated internally or externally by securing the ground lug 6 at a suitable location along one of the symmetrically arrayed channels 8 or 9 using a screw and nut. FIGS. 1 and 2 also show the location of an ozone outlet conduit 4, which will be further described in relation to FIGS. 4 and 11.

Description of Mounting Tabs

Figure 5:
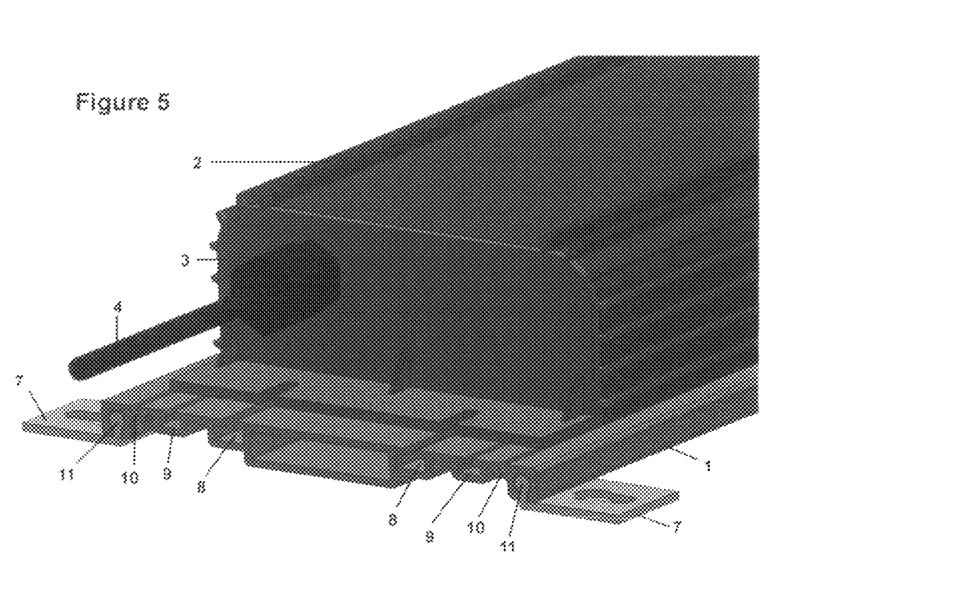
FIG. 5 is a perspective view of the output end of the ozone generator, showing the features of the base, channels, cover, end cap, outlet and optional mounting tabs.
Figures 9, 10, 11:
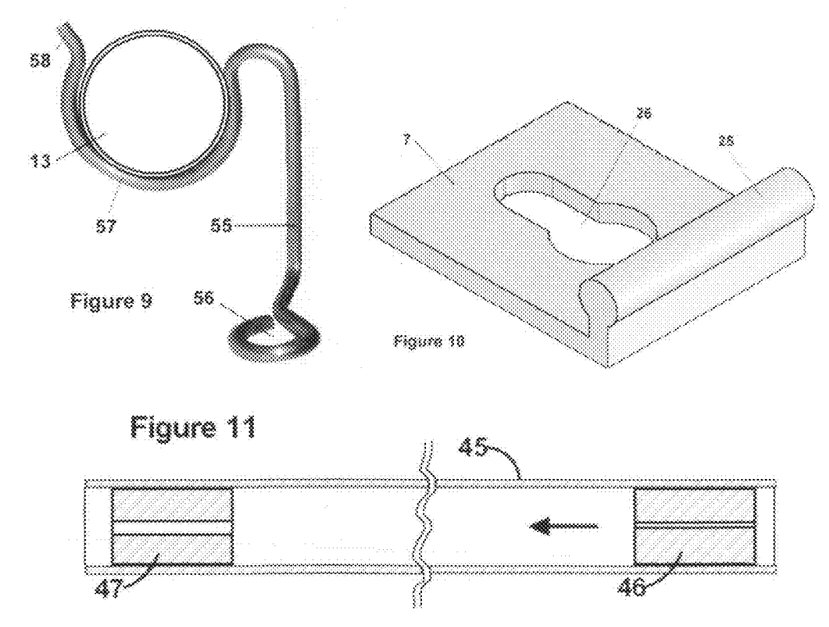
FIG. 9 shows one of two lamp clips used to mount the ultraviolet bulbs to the base.
FIG. 10 is a detailed view of one of the mounting tabs shown in FIGS. 1-2 and 5-7.
FIG. 11 is a sectional view of the ozone outlet conduit showing the flow restrictor and the back flow restrictor located therein.

The ozone generator optionally includes adjustable mounting tabs 7 that slide within at least one of the channels 11 that extend along the bottom edges of the base 1, as best shown in FIG. 5. As shown in FIG. 10, the tabs 7 are segments of an extrusion that have been punched to form a keyhole 26 to receive a mounting screw or bolt during installation. The tabs 7 also include a rail 25 that is sized to slide smoothly within the channels 11. The position of the mounting tabs 7 within channels 11 can be easily adjusted in the field, allowing the ozone generator 41 to be mounted on or between points on almost any surface or structure.

Description of Cover

Figure 3:
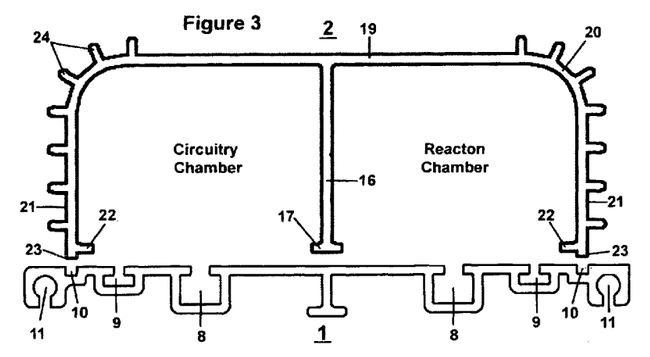
FIG. 3 is an end view of the cover and base in proximate locations and aligned for engagement.

Referring to FIGS. 2 and 3, the cover 2 includes a co-extruded partition or baffle 16 running its entire length. When the cover 2 is in place over the base 1, the baffle 16 divides the internal portion of the ozone generator 41 into two separate chambers: a reaction chamber that contains the sources of ultraviolet light and a circuitry chamber that contains the electronic components.

As best shown in FIG. 3, the cover 2 includes a top 19 which transitions through shoulders 20 into opposing sidewalls 21. Each sidewall 21 terminates in a lower edge 23 and offset flange 22. The partition or baffle 16 terminates in a twin flange 17. When the cover 2 is fully engaged over the base I the edges 23 of both sidewalls 21 fit into channels 10 and the bottom surface of the twin flange 17 is in close contact with the upper surface of the base 1, thereby defining the circuitry and reaction chambers referred to above and shown in FIG. 3.

The cover 2 also includes a number of ribs 24 spaced from the outer portion of the top surface 19 to above the edge 23. These ribs 24, which extend over the entire length of the cover 2, serve a number of purposes: they provide rigidity to the structure, they limit deformation of the extrusion, they provide radiation to dissipate heat generated by the enclosed bulbs and they provide a gripping mechanism for removing and installing the cover 2 on the base 1. The top surface 19 is preferably flat to receive labeling and other printed or engraved indicia.

Description of Base

FIG. 3 also shows a detailed end view of the extruded base 1 with the integrally formed channels 8, 9, 10 and 11. There are two sets of these channels symmetrically disposed in relation to the centerline of the base 1. As described above, channel 11 receives the mounting tabs 7 and channel 10 receives the edges 23 of the cover 2. Channels 8 and/or 9 are used to secure both of the end caps 3, the switch assembly 15 the ballasts 14 the ground lug 6 and, as further described in relation to FIG. 9, the bulb clips 55 used to detachably mount the bulbs 13 to the base 1.

The channels 8 are configured to receive and prevent rotation of either a bolt head or a nut (preferably square). When the head of a bolt is engaged in a channel 8, the threaded portion of the bolt extends upward through the continuous slot into one of the two chambers that are defined and separated by the baffle 16. To make a connection the threaded portion of the bolt extends through a slot or aperture in the structure to be secured and a nut, threaded on the end of the bolt, is tightened to secure the structure to the base. Alternatively, a nut can be engaged in channel 8 and a bolt, extending from above the base I can be threaded into the nut to secure the structure. Since channel 8 is deeper than the thickness of a standard nut, a tightened bolt can draw the nut firmly to the top of the channel and the end of the bolt can extend beyond the nut into the lower portion of the channel.

The channels 9 are relatively shallow and, while they can be used to receive the head of a bolt with its threads extending upward into one of the chambers, they are also used to receive parallel T-rails formed on the bottom of each end cap 3 (not shown). These T-rails allow the end caps 3 to slide into and out of engagement with the cover 3 during manufacture and maintenance of the ozone generator 41. In all cases the structures to be secured can be located anywhere along the length of the base and the attachment process can be accomplished solely by working from the top of the base 1, using either a screwdriver or a nut driver.

The assembly process is facilitated by pre-assembling the nut onto the end of the bolt before sliding the combination into one of the channels 8. As shown in the drawings, the bases of the end caps 3 and the ballasts 14 are slotted and can be easily connected without disassembling the nut and bolt. Both the switch assembly (FIG. 12) and the lamp clip (FIG. 9), have mounting holes (items numbered 50 and 56 respectively) rather than slots. These components can be easily installed by first loosely assembling a bolt and nut through the mounting hole and then sliding the combination into the desired channel 8 to the desired location on the base 1.

Description of Lamps

In the dual-bulb embodiment of the invention shown in FIG. 2, the cover 2 is approximately 17 inches in length. This same configuration can also accommodate a single bulb 13 and single ballast 14 for use in applications requiring a lower volume of ozone output. High intensity ultraviolet bulbs, which are more expensive and are often characterized by shorter useful lives, can be used in both the single-bulb and dual-bulb embodiments. High intensity bulbs generally have the same dimensions as regular bulbs.

Lower capacity ultraviolet bulbs are also available in shorter lengths. These shorter bulbs can be incorporated into the ozone generator 41 in both a single-bulb and dual-bulb configurations. Both of these shorter configurations dictate the use of a cover 2 that is approximately 11 inches in length. This version of the invention is particularly adapted for use on free-standing spas and hot tubs as well as fish tanks and air-injection systems. Ultraviolet bulbs suitable for use in the present invention are available from a number of domestic and foreign manufacturers and suppliers. For example, the bulbs used in the commercial version of the present invention were supplied by Atlantic Ultraviolet of Hauppauge, N.Y.

FIG. 9 shows a wire-formed clip 55 that is inexpensive and works well in supporting the ultraviolet bulbs 13 used in various embodiments of the invention. One end of the clip 55 is formed into a connection loop 56 which receives a screw that secures the clip at an appropriate location along one of the channels 8 in base. The other end of the clip 55 is formed into a partial, bulb-retention loop 57 which is characterized by (a) a diameter approximately equal to that of the bulbs to be retained (nominally 0.75 inches), (b) just over 180 degrees of included arc, (c) a spatial orientation that is at ninety degrees with respect to the plane of connection loop 56, and (d) a short terminal segment 58 that can be slightly displaced to open the loop 57 to release the bulb 13.

Since the extruded lengths from which the base 1 and cover 2 are cut typically come in lengths between 12 and 24 feet, individual parts can be cut to the desired length based on actual demand. The end caps 3 work equally well with any of the at least eight alternative configurations possible with available bulbs (normal or high-intensity, regular or short length, single- or dual-bulb). This wide degree of adaptability eliminates the need for multiple special configurations and reduces the costs associated with manufacture and inventory maintenance.

While light emitting diodes can be fabricated to emit light in the 185 nm range, this form of ultraviolet light source is not currently available at commercial pricing levels. However, when these and other solid state light sources become generally available, they can be readily incorporated into even shorter, less expensive and more efficient embodiments of the present invention, all without the need for retooling.

Description of Ozone Outlet

Figure 4:
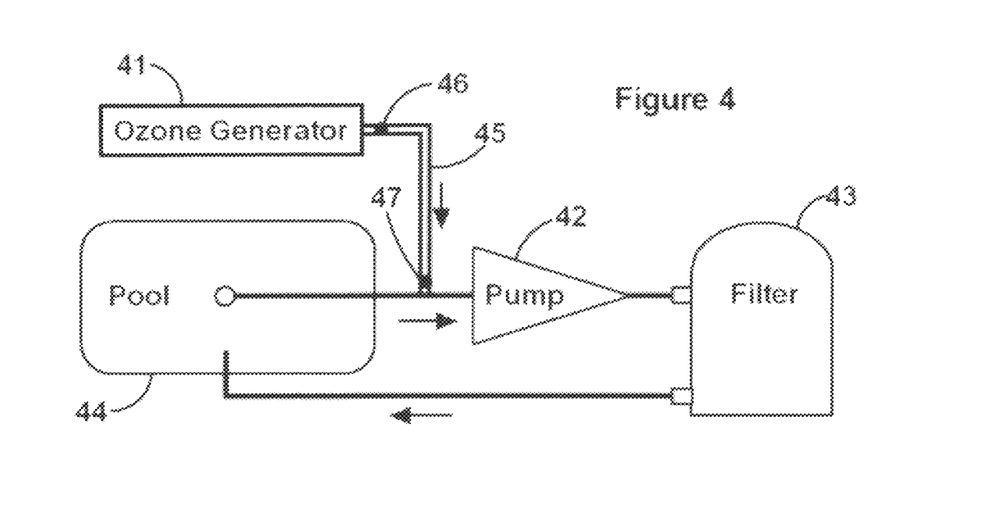
FIG. 4 is a diagram showing the elements of a simple swimming pool water circulation system and the functional relation of the ozone generator to that system.

The ozone generator 41 can be used in many different applications. One area of highly effective application involves water circulation systems installed on residential swimming pools. FIG. 4 shows the simplest form of swimming pool circulation system, which includes a swimming pool 44 from which water is circulated by an electric motor driven pump 42 through a filter 43 and back into the pool. The electric motor is typically controlled by a timer (not shown), which limits operation to certain limited periods during any 24-hour cycle of operation.

In the general application of FIG. 4, the ozone generator 41 is connected to the inlet side of the pump 42 by a conduit or tube 45 which defines a flow path between the two. Suction from the pump draws ozone from the generator 41 into the circulating water were it oxidizes microorganisms, particulates, and other organic matter in the water. The oxidation of these pollutants inactivates living matter and improves filter effectiveness by binding smaller particulates and creating larger, more filterable particles.

The amount of ozone that is injected into the swimming pool circulation system can be controlled by a simple restrictor inserted in conduit 45 to limit the flow between the generator and the inlet to pump 42. For example, where the conduit 45 is a tube having a 0.25" diameter, a flow restrictor 46 having a 0.020" inside diameter may be inserted into the flow path 45 distal to the generator output. The purpose of the 0.020" restrictor 46 is to limit the amount of ozone that can be drawn into the circulation system by the pump 42. If too much ozone is delivered it may result in cavitation at the pump, resulting in a loss of circulation efficiency and possible damage to the pump impeller. If too little ozone is injected into the circulating water, there will not be a sufficient volume to effectively perform the desired oxidization/disinfection processes.

The cross-sectional view of FIG. 11 shows a segment of conduit 45, including the flow restrictor 46. A back-flow restrictor 47, having an inside diameter of approximately 0.040", is also located within the flow path 45, before it joins with the inlet to pump 42. The purpose of the 0.040" restrictor 47 is to prevent water from pulsing into flow path 45 and toward the generator 41 during transient back pressure pulses caused, for example, by the flow inertia immediately following the shut down of pump 42. Preferably, the two restrictors 46 and 47 are located within approximately 6" of one another in a short segment of line 4 that extends from the end cap 3 as shown in FIG. 5. In the field, an additional length of tubing can be use to connect the ozone outlet 4 to the inlet of the pump 42.

Description of Wiring

Figure 7:
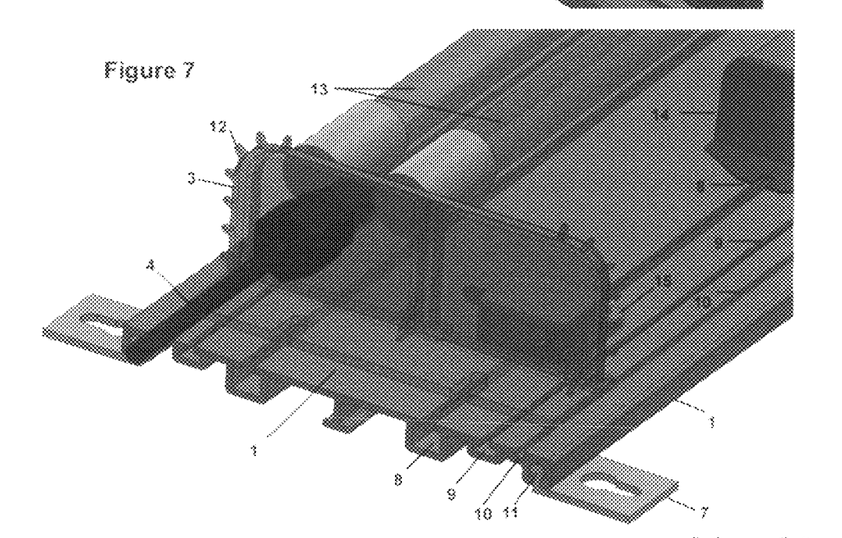
FIG. 7 is a rotated perspective view of the same area shown in FIG. 6, with the end cap appearing partially transparent.
Figure 8:
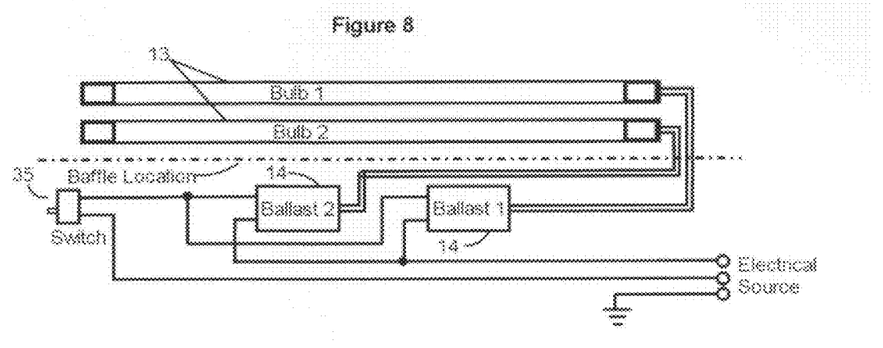
FIG. 8 is a circuit diagram showing the wiring of the components shown in FIG. 2 and the general location of the baffle that separates the reaction chamber from the circuitry chamber.

The wiring diagram of FIG. 8 shows the simple interconnection of the bulbs and electrical components of the preferred embodiment shown in the drawings. The layout of FIG. 8 generally corresponds to the physical location of the corresponding elements shown in FIGS. 2, 5-7 and 13. The electrical source (e.g., 110 or 220 VAC) is connected in parallel across the inputs to the two ballasts 14, with one line interrupted by the position-sensitive micro switch 35. The output lines from each of the two separate ballasts are connected to the corresponding bulb inputs. While FIG. 8 shows a dual-bulb system, the wiring of a single-bulb system is the same, only the leads to and from the second ballast are eliminated.

The electrical function of the switch 35 is to detect an opening of the enclosure formed by the base 1, the cover 2 and the end caps 3. During normal operation, the position-sensing arm or plunger which controls the on/off state of switch 35 is contracted and the switch is in the on or conductive state. The switch 35 remains in this state until the end cap 3 that is in contact with switch 35 is moved slightly outward causing the position sensing arm or plunger to extend toward its normally open position, breaking the circuit between the electrical source and the two ballasts 14. Switch 35 performs a two-part safety function by detecting when the enclosure is open or about to open and turning off the bulbs 13 in response to the detected condition. Turning off the bulbs 13 terminates the generation of ozone and prevents any eye or skin damage that might result from significant exposure to ultraviolet radiation.

Description of Switch Assembly

Figure 6:
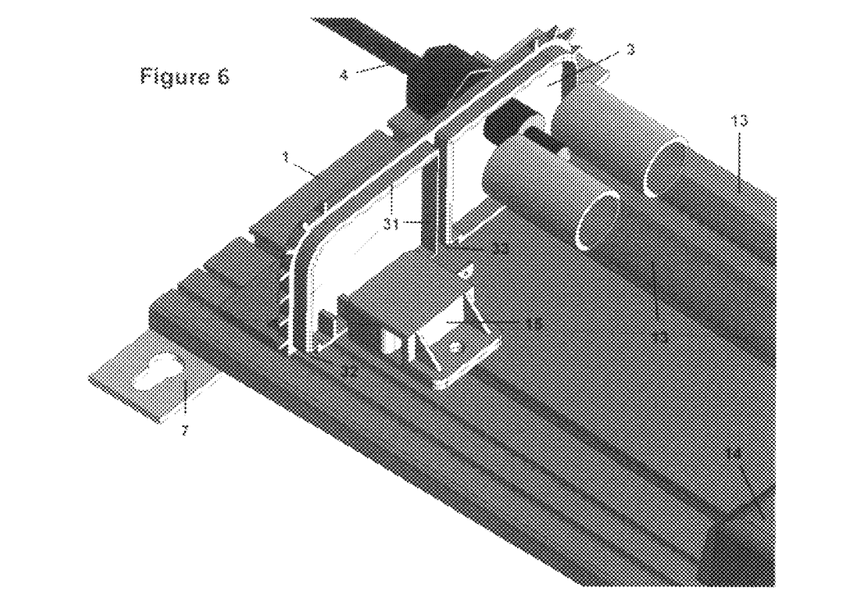
FIG. 6 is a perspective view of the output end of the ozone generator showing the inner features of the end cap and the relative locations of the ozone outlet, switch assembly, bulbs, ballast, tabs and channels.
Figure 12:
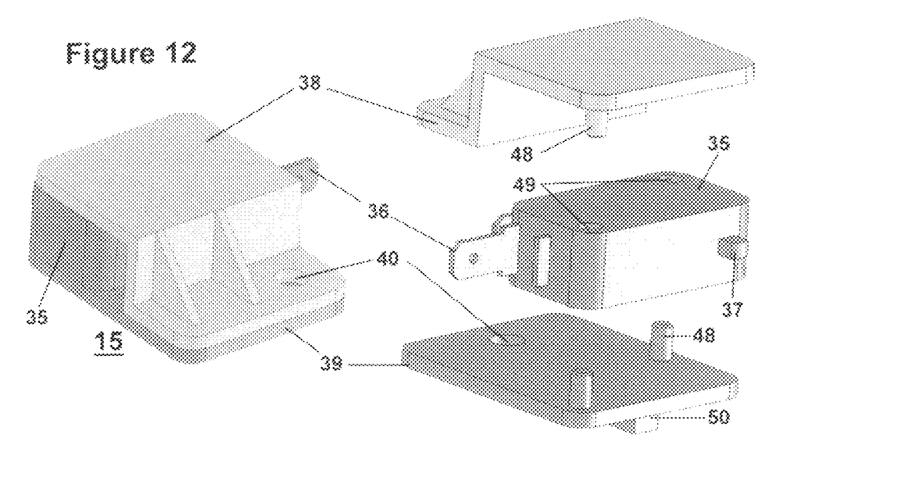
FIG. 12 shows the switch assembly (left) and the components thereof (exploded, right).
Figure 13:
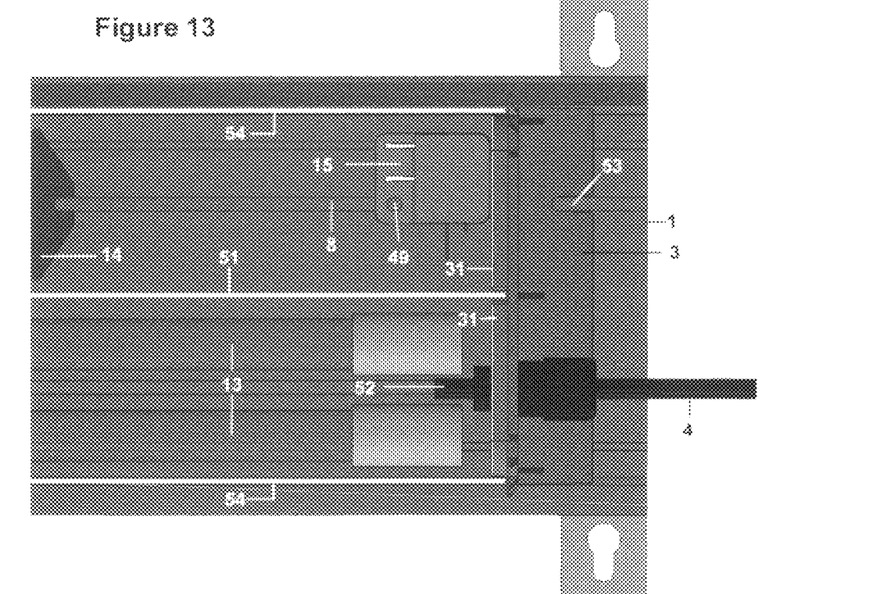
FIG. 13 is a plan view of the switch assembly installed in relation to the end cap, with lines added to indicate the location of the cover's sidewalls and baffle.

The switch assembly 15 is generally depicted in FIGS. 2, 6 and 7 and shown in detail in FIG. 12 and in the plan view of FIG. 13. The complete assembly 15 is shown on the left of FIG. 12 and the three components are shown individually in the exploded view on the right of FIG. 12. The micro switch 35 includes an actuator 37 that closes the internal contacts when depressed and opens the internal contacts when extended as shown in FIG. 12. In traditional terms this is a normally-open, single-pole, single-throw micro switch. Switch 35 further includes connector points 36 and mounting holes 49.

Accurately and positively positioning the switch 35 during assembly of the ozone generator 41 is often sensitive and difficult. To assure precise positioning, the switch 35 is mounted between an upper retainer 38 and a lower retainer 39. Both of the retainers 38 and 39 include alignment pins 48 that fit closely into mounting holes 49 in the body of switch 35 and prevent lateral and rotational motion between the components. The lower retainer 39 includes a rail 50 that fits and slides in the open slot at the top of channel 8 or 9 on base 1.

The switch assembly 15 is secured to base I by extending a screw through the holes 40 in the upper and lower retainers 38 and 39 and securing the screw to a nut retained within one of the channels 8 or 9. This arrangement allows the switch assembly to be moved within one of the channels to a precise location and then firmly secured by tightening the screw through holes 40, while the rail 50 prevents transverse and rotational movement.

FIG. 13 is a plan view of the base 1 with end cap 3 and switch assembly 15 in their final positions. The actuator 37 depressed and the switch 35 is in its conductive state. The central line 51 indicates the installed location of baffle 16. The two outer lines 54 indicate the location of the sidewall edges 23 of cover 2 (FIG. 3). As can be seen in FIG. 13, the internal ribs 31 on end cap 3 extend into the area between the sidewalls 21 of cover 2 and the baffle 16, closing off the end of cover 2. When the end cap 3 is slightly moved out of this engagement with the cover 3, the actuator 37 on switch 35 moves outward, breaking the circuit to the ballasts 14 and turning off the bulbs 13.

Description of End Caps

As seen in FIG. 6, the end caps 3 have two sets of internal ribs 31 that closely conform to the inner surfaces of the cover 2 and provide a tight closure of the opening between the ends of the cover 2 and the base 1. The vertical portions of the ribs 31 in the center of the end cap are spaced apart and define a vertical retention slot that receives the end of the baffle 16. At the bottom of this retention slot the ribs are offset to form a horizontal slot 33 to receive and retain the flange 17 located at the bottom of baffle 16 (FIG. 3). The ribs 31 are also offset on both sides of the end cap to form slots 32 that receive the flanges 22 extending inward from the sidewalls 21 of the cover 2 (FIG. 3).

Figure 14:
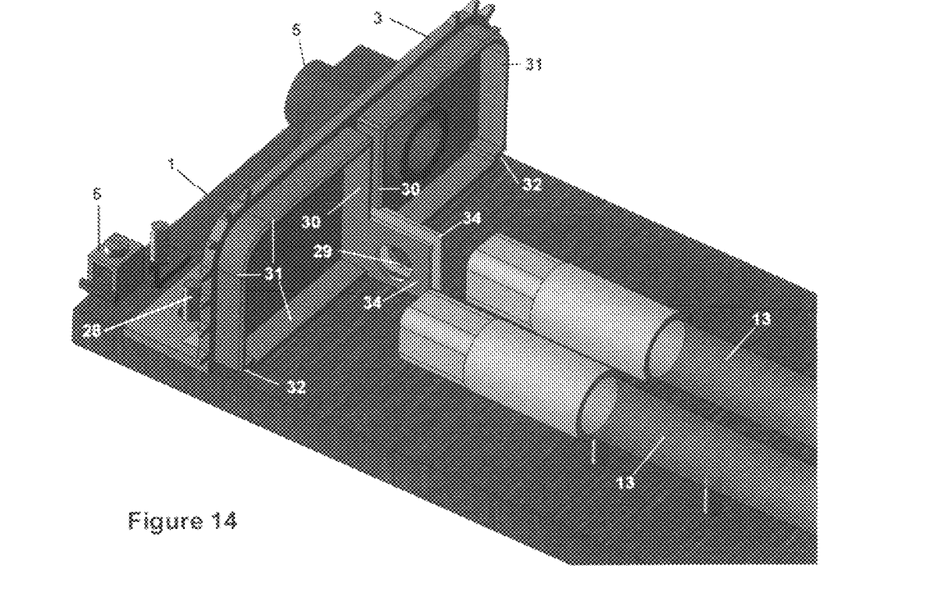
FIG. 14 is a perspective view of the fixed end of the ozone generator showing the inner features of the end cap and the wire retention structures molded as an integral part thereof.

As illustrated in FIG. 14, the end cap 3 that includes the electrical feed through 5 also includes internal ribs 31 that closely conform to and engage the inner surfaces of the cover 3. In FIG. 14 this end cap further includes adjacent wire retainers 34 that are partial extensions of the two central ribs 30. Each of the wire retainers 34 includes a hole 29 that receives the electrical wires connecting the bulbs 13 in the reaction chamber to the corresponding baffles 14 in the circuitry chamber. The retainers 34 hold the lamp wires in position when the cover 2 is placed over or removed from the ozone generator 41.

In the preferred assembly of the ozone generator 41, the end cap 3 shown in FIG. 14 is first engaged on the base 1 by sliding the two parallel T-rails formed on the bottom of the end cap into channels 9 and moving it to the desired position. The end cap is then secured in this position, permanently or semi-permanently, by means of rivets or tamper-proof screws joining the two slotted portions of the end cap firmly to the channel 8 formed in the base 1. This fixed end cap 3 provides a reference for the placement of other components, particularly the switch assembly 15 and the end cap 3 located at the opposite end of the ozone generator. The precise location of these other components will vary depending on the finished length of the cover 2, but any variations can be easily accommodated by the longitudinal adjustability made possible by the channel connection system.

Figure 15:
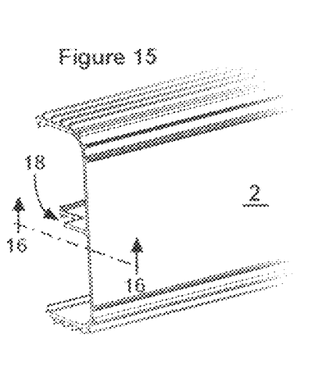
FIG. 15 is a perspective view of the end of the cover showing the location of the notch that provides clearance for wiring between the internal chambers.
Figure 16:
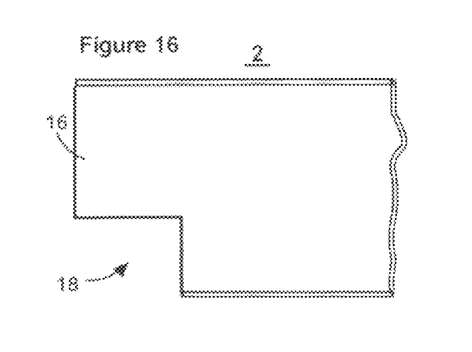
FIG. 16 is a sectional view taken at section 16-16 in FIG. 15.

To accommodate the wires passing through holes 29 (FIG. 14) from the circuitry chamber to the reaction chamber, it is necessary to create a notch 18 in the baffle 16, as shown in the perspective view of FIG. 15 and in the sectional view of FIG. 16. During final assembly of the ozone generator 41, when the cover 2 is installed over the base 1, its edges 23 are placed in channels 10 (FIG. 3) and the cover 3 is moved into full engagement over the internal ribs 31 on the end cap 3 shown in FIG. 14. The upper portion of baffle 16 is retained between the two central ribs 30 and the notch 18 (FIGS. 15 and 16) provides clearance for the wires passing through holes 29 in wire retainers 34. The flanges 22 on the cover 2 (FIG. 3) slide into and are retained by slots 32 formed at the bottom of the outer ribs 31. The slots 32 cooperate with flanges 22 to prevent vertical displacement of this end of the cover 2.

When the opposing end cap 3 (FIGS. 6 and 7) is secured in position, corresponding slots 32 and 33 retain flanges 22 and 17 (FIG. 3) and prevent vertical displacement of that end of the cover 2. The end cap 3 shown in FIGS. 6 and 7 is fixed to the base 1 by means of two T-rails on the under side of the end cap. These T-rails allow the end cap 3 to move longitudinally in and out of engagement with the cover 2 without becoming detached from the base 1. When in its final position, this end cap is further secured in position by detachable connections through the two slots and into channels 8. As the end cap 3 shown in FIGS. 6 and 7 slides on its T-rails into full engagement with the adjacent end of cover 2, the actuator 37 on switch 35 is depressed, allowing the bulbs 13 to be energized when the power to the ozone generator is activated. With both end caps 3 secured to the base 1, displacement of the cover 2 is fully restricted.

Installation of the ozone generator 41 involves mounting the device in a suitable location using the adjustable tabs 7, connecting the ozone outlet 4 (which includes the restrictors 46 and 47 shown in FIG. 11) to the ozone injection point (FIG. 4) and connecting the electrical leads to an appropriate electrical source (FIG. 8). Servicing the internal components of the ozone generator 41 can be accomplished by loosening the screws that retain the end cap 3 shown in FIGS. 6 and 7, sliding the end cap toward the adjacent end of the base 1, and disengaging the cover 2 from the opposing end cap 3 shown in FIG. 14.

What I claim is:

1. An improved ozone generator for use in purification systems, comprising in combination:
   (a) an extruded base having a plurality of longitudinal channels for receiving connections at distributed points;
   (b) an extruded cover having a top surface that transitions by curved shoulders to two side walls for engaging said base adjacent to each opposing side thereof and for covering a substantial portion of said base, said cover being detachably connectable to said base;
   (c) a longitudinal baffle dividing the volume between said base and said cover into a reaction chamber and a circuitry chamber;
   (d) at least one ultraviolet light source for converting oxygen in ambient air into useable amounts of ozone, said light source being mounted to connection points on one of said longitudinal channels within said reaction chamber;
   (e) electronic circuitry for controlling and transforming an input voltage to drive said light source, said circuitry being mounted to connection points on one of said longitudinal channels within said circuitry chamber;
   (f) removable end caps for separately covering apertures formed by the ends of said cover and said base, said end caps being connected to said base by means of at least two of said channels;
   (g) an outlet conduit providing fluid communication between from the reaction chamber, said conduit being selectively restricted to control the fluid flow therein.

2. The generator of claim 1 wherein the baffle is extruded as an integral part of said cover.

3. The generator of claim 2 wherein the cover is detachably connected to the base by means incorporated in each of said end caps.

4. The generator of claim 3 wherein the end caps include at least one rail that slides in one of the channels formed in said base.

5. The generator of claim 4 further including
   a position-sensitive switch for disconnecting the input voltage from the light source in response to a predetermined change in position of one of the surfaces enclosing said reaction chamber.

6. The generator of claim 5 wherein the switch is adjustably mounted to at least one of the channels located within the circuitry chamber and is electrically closed when one of said end caps is in its fully engaged position between the cover and the base.

7. The generator of claim 6 further including
   a plurality of mounting tabs moveably engaged within at least one channel on said base for mounting said base to a support structure at one or more distributed connection points.

8. A method for making an improved ozone generator for use in purification systems, including the steps of:

(a) extruding a base having a plurality of longitudinal channels for receiving connections at distributed points along the length of said base;
(b) extruding a generally channel-shaped cover for detachable connection to said base, said cover having a top surface that transitions by curved shoulders to two side walls for engaging said base along opposing sides thereof;
(c) producing a longitudinal baffle for dividing the volume between said base and said cover into a reaction chamber and a circuitry chamber;
(d) detachably mounting at least one ultraviolet light source to connection points on one of said longitudinal channels within the area of said reaction chamber, said light source being capable of converting oxygen in ambient air into useable amounts of ozone;
(e) mounting electronic circuitry to connection points on one of said longitudinal channels within the area of said circuitry chamber; said circuitry being capable of controlling and transforming an input voltage to drive said light source for conversion of oxygen to ozone;
(f) molding end caps for separately covering the opposing apertures formed by the ends of said cover and said base;
(g) providing an outlet conduit from the reaction chamber for connection to a point of ozone injection, said conduit including at least one restriction to control the fluid flow therein;
(h) providing electrical conductors between the electronic circuitry and an electrical power source;
(i) securing said baffle between the reaction and circuitry chambers and between said end caps;
(j) engaging the cover in position on the base;
(k) connecting said end caps to at least two channels on said base to enclose the apertures formed by the ends of the cover and the base; and,
(l) detachably connecting said cover to said base.

9. The method of claim 8 wherein said baffle is produced as an integral part of said extruded cover and is secured between said reaction and circuitry chambers concurrently with said cover being engaged in position on said base.

10. The method of claim 9 wherein said cover is detachably connected to said base by retention structures incorporated in said end caps and steps (k) and (l) are performed substantially concurrently.

11. The method of claim 10 wherein the connection of said end caps is carried out in part by rails formed on the bottom of said end caps allowing them to slide in at least one of the channels formed in said base.

12. The method of claim 11 including the intermediate step of
installing a position-sensitive switch for disconnecting the input voltage from the light source in response to a predetermined change in position of a surface enclosing said reaction chamber.

13. The method of claim 12 wherein the switch is adjustably mounted to at least one of the channels located within the circuitry chamber and is electrically closed when one of said end caps is in its fully engaged position between the cover and the base.

14. An ozone generator made by the method of claim 13.

15. The method of claim 13, including the further steps of:
(o) securing the base to a support structure by means of said plurality of adjustable mounting tabs secured in at least one of the channels;
(p) connecting the outlet conduit to an ozone injection point;
(q) connecting the electrical lines to a source of electrical power;
(r) selectively driving the light source to generate ozone in the reaction chamber; and,
(s) drawing ozone from the reaction chamber to the point of ozone injection.

16. The method of claim 15, including the further steps of:
(t) accessing the light source and electrical circuitry for maintenance by (i) disengaging at least one of the end caps from the cover, and (ii) removing the cover from its engaged position on the base.

* * * * *